US011211249B2

(12) United States Patent
Hughes et al.

(10) Patent No.: US 11,211,249 B2
(45) Date of Patent: Dec. 28, 2021

(54) HERBAL EXTRACTS AND FLAVOR SYSTEMS FOR ORAL PRODUCTS AND METHODS OF MAKING THE SAME

(75) Inventors: Kenneth John Hughes, Furneux Pelham (GB); Sylvia Gaysinsky, Zionville, IN (US); Roger Michael Browning, Milton Keynes (GB)

(73) Assignee: Sensient Flavors LLC, Indianapolis, IN (US)

( * ) Notice: Subject to any disclaimer, the term of this patent is extended or adjusted under 35 U.S.C. 154(b) by 110 days.

(21) Appl. No.: 13/490,206

(22) Filed: Jun. 6, 2012

(65) Prior Publication Data
US 2012/0244084 A1 Sep. 27, 2012

Related U.S. Application Data

(63) Continuation of application No. 12/399,295, filed on Mar. 6, 2009, now abandoned.

(60) Provisional application No. 61/034,455, filed on Mar. 6, 2008, provisional application No. 61/034,908, filed on Mar. 7, 2008, provisional application No. 61/034,902, filed on Mar. 7, 2008, provisional application No. 61/073,640, filed on Jun. 18, 2008.

(51) Int. Cl.
*A61K 31/35* (2006.01)
*H01L 21/265* (2006.01)
*H01L 21/223* (2006.01)
*H01L 29/66* (2006.01)
*H01L 29/78* (2006.01)

(52) U.S. Cl.
CPC .... *H01L 21/26506* (2013.01); *H01L 21/2236* (2013.01); *H01L 21/2658* (2013.01); *H01L 29/6659* (2013.01); *H01L 29/7833* (2013.01); *H01L 21/26513* (2013.01)

(58) Field of Classification Search
None
See application file for complete search history.

(56) References Cited

U.S. PATENT DOCUMENTS

| | | |
|---|---|---|
| 2,571,948 A | 10/1951 | Sair et al. |
| 3,627,540 A | 12/1971 | Katz et al. |
| 3,746,553 A | 7/1973 | Anderson |
| 3,821,417 A | 6/1974 | Westall et al. |
| 3,947,570 A | 3/1976 | Pensak et al. |
| 4,045,581 A | 8/1977 | Mackay et al. |
| 4,045,587 A | 8/1977 | Katz et al. |
| 4,123,559 A | 10/1978 | Vitzhum et al. |
| 4,136,065 A | 1/1979 | Vano et al. |
| 4,157,401 A | 6/1979 | Stroz et al. |
| 4,158,708 A | 6/1979 | Chiovini et al. |
| 4,198,432 A | 4/1980 | Vitzthun et al. |
| 4,208,431 A | 6/1980 | Friello et al. |
| 4,217,368 A | 8/1980 | Witzel et al. |
| 4,223,003 A | 9/1980 | Scheller |
| 4,238,475 A | 12/1980 | Witzel et al. |
| 4,238,510 A | 12/1980 | Cherukuri et al. |
| 4,250,196 A | 2/1981 | Friello |
| 4,301,178 A | 11/1981 | Witzel et al. |
| 4,316,915 A | 2/1982 | Friello et al. |
| 4,344,972 A | 8/1982 | Wienecke |
| 4,380,506 A | 4/1983 | Kimura et al. |
| 4,423,030 A | 12/1983 | Hayes et al. |
| 4,431,680 A | 2/1984 | Yoshida |
| 4,465,661 A | 8/1984 | Schmolka |
| 4,476,107 A | 10/1984 | Schmolka |
| 4,476,142 A | 10/1984 | Netherwood et al. |
| 4,478,864 A | 10/1984 | Blackwell et al. |
| 4,490,398 A | 12/1984 | Behr et al. |
| 4,548,809 A * | 10/1985 | Fung .................. A61K 8/21 |
| | | 424/49 |
| 4,606,849 A | 8/1986 | Ansari et al. |
| 4,612,205 A | 9/1986 | Kupper et al. |
| 4,632,837 A | 12/1986 | Schutz et al. |
| 4,632,937 A | 12/1986 | Lynch |
| 4,716,035 A | 12/1987 | Sampathkumar |
| 4,735,358 A | 4/1988 | Morita et al. |
| 4,775,537 A | 10/1988 | Calabro et al. |
| 4,803,082 A | 2/1989 | Cherukuri et al. |
| 4,835,002 A | 5/1989 | Wolf et al. |
| 4,877,635 A | 10/1989 | Todd, Jr. |

(Continued)

FOREIGN PATENT DOCUMENTS

| | | |
|---|---|---|
| CA | 2143037 | 11/1995 |
| CN | 1319418 A * | 10/2001 |

(Continued)

OTHER PUBLICATIONS

Zekovic et al., Tablets with Thyme (*Thymus vulgaris* L.) Extracts, 2002, BIBLID, 33: 159-165.*
Moyler (1993, Extraction of flavours and fragrances with compressed CO2, pp. 140-183.*
Bestmann, H.J. et al., "Extraction of thyme with liquid CO2 on a laboratory scale," Zeitschrift Fuer Lebensmittel-Untersuchung und Forschung, (1985) 180(6):491-493.
Borrett, J., "Carbon dioxide—a liquid asset!" Innovations in Food Technology (2005) 2 pages.
Jolly, D.R.P., "Wine flavour extraction with liquid carbon dioxide," Process Biochemistry (1981) 16(5):36-40.

(Continued)

*Primary Examiner* — Terry A McKelvey
*Assistant Examiner* — Catheryne Chen
(74) *Attorney, Agent, or Firm* — Michael Best & Friedrich LLP (57) ABSTRACT

The invention provides a method for preparing an herbal extract and a flavor system comprising an herbal extract produced by the process. The invention also provides a flavor system comprising an herbal extract comprising thymol, eugenol, carvacrol and eucalyptol. The invention further provides a flavor system comprising a thyme extract having a minimum inhibitory concentration of less than about 3%. Additionally, the invention provides an oral product comprising a flavor system.

6 Claims, 5 Drawing Sheets

(56) References Cited

U.S. PATENT DOCUMENTS

| | | |
|---|---|---|
| 4,919,149 A | 4/1990 | Stang |
| 4,923,685 A | 5/1990 | Wuelknitz et al. |
| 4,923,865 A | 5/1990 | Cossement et al. |
| 4,925,688 A | 5/1990 | Voituriez |
| 4,935,104 A | 6/1990 | Coutiere |
| 4,945,087 A | 7/1990 | Talwar et al. |
| 4,946,695 A | 8/1990 | Forster et al. |
| 4,983,394 A | 1/1991 | Hussein et al. |
| 4,985,265 A | 1/1991 | Duboc et al. |
| 4,990,329 A | 2/1991 | Sampathkumar |
| 4,994,262 A | 2/1991 | Charbonneau et al. |
| 5,015,464 A | 5/1991 | Strobridge |
| 5,017,397 A | 5/1991 | Nguyen et al. |
| 5,023,020 A | 6/1991 | Machida et al. |
| 5,030,459 A | 7/1991 | Barcelon et al. |
| 5,032,387 A | 7/1991 | Hill et al. |
| 5,043,153 A | 8/1991 | Videki et al. |
| 5,063,070 A | 11/1991 | Klemann et al. |
| 5,064,668 A | 11/1991 | Klemann et al. |
| 5,091,117 A | 2/1992 | Athnasios et al. |
| 5,093,145 A | 3/1992 | Darbonne et al. |
| 5,094,843 A | 3/1992 | Mazzonobile et al. |
| 5,110,583 A | 5/1992 | Sampathkumar |
| 5,110,608 A | 5/1992 | Cherukuri et al. |
| 5,120,558 A | 6/1992 | Nguyen et al. |
| 5,227,183 A | 7/1993 | Aung et al. |
| 5,277,910 A | 1/1994 | Hidvegi |
| 5,298,238 A | 3/1994 | Hussein et al. |
| 5,338,558 A | 8/1994 | Aung et al. |
| 5,356,615 A | 10/1994 | Gaffar |
| 5,403,587 A | 4/1995 | McCue et al. |
| 5,433,949 A | 7/1995 | Kahleyss et al. |
| 5,437,879 A | 8/1995 | Kabse et al. |
| 5,458,890 A | 10/1995 | Williford et al. |
| 5,472,685 A | 12/1995 | Gaffar |
| 5,487,902 A | 1/1996 | Andersen et al. |
| 5,512,285 A | 4/1996 | Wilde |
| 5,525,260 A | 6/1996 | Aeschbach et al. |
| 5,527,552 A | 6/1996 | Todd, Jr. |
| 5,585,343 A | 12/1996 | McGee et al. |
| 5,616,358 A | 4/1997 | Taylor |
| 5,633,027 A | 5/1997 | Cherukuri et al. |
| 5,679,389 A | 10/1997 | Wong et al. |
| 5,698,181 A | 12/1997 | Luo |
| 5,702,687 A | 12/1997 | Miskewitz |
| 5,723,106 A | 3/1998 | Buch et al. |
| 5,811,080 A | 9/1998 | Burgess et al. |
| 5,817,295 A | 10/1998 | Chaudhari et al. |
| 5,820,852 A | 10/1998 | Burgess et al. |
| 5,849,269 A | 12/1998 | Burgess et al. |
| 5,853,726 A | 12/1998 | Chevereau |
| 5,858,370 A | 1/1999 | Deans et al. |
| 5,858,446 A | 1/1999 | Lewis et al. |
| 5,891,422 A | 4/1999 | Pan et al. |
| 5,900,230 A | 5/1999 | Cutler |
| 5,939,050 A | 8/1999 | Iyer et al. |
| 5,939,071 A | 8/1999 | Joseph |
| 5,942,211 A | 8/1999 | Harper et al. |
| 5,942,244 A | 8/1999 | Friedmann et al. |
| 5,948,439 A | 9/1999 | Forman et al. |
| 5,955,086 A | 9/1999 | Deluca et al. |
| 5,965,518 A | 10/1999 | Nakatsu et al. |
| 5,980,869 A | 11/1999 | Sanker et al. |
| 5,985,345 A | 11/1999 | Todd |
| 5,985,352 A | 11/1999 | Todd |
| 6,013,304 A | 1/2000 | Todd |
| 6,022,551 A | 2/2000 | Jampani et al. |
| 6,027,716 A | 2/2000 | Levin et al. |
| 6,042,812 A | 3/2000 | Sanker et al. |
| 6,123,945 A | 9/2000 | Nakatsu et al. |
| 6,169,118 B1 | 1/2001 | Bilali |
| 6,235,267 B1 | 5/2001 | Delli Santi et al. |
| 6,235,318 B1 | 5/2001 | Lombardy, Jr. et al. |
| 6,245,309 B1 | 6/2001 | Etievant et al. |
| 6,248,309 B1 | 6/2001 | Iyer et al. |
| 6,248,343 B1 | 6/2001 | Jampani et al. |
| 6,294,186 B1 | 9/2001 | Beerse et al. |
| 6,315,987 B1 | 11/2001 | Plochocka |
| 6,322,838 B1 | 11/2001 | Guntert et al. |
| 6,338,861 B1 | 1/2002 | Gozu et al. |
| 6,346,281 B1 | 2/2002 | DeAth et al. |
| 6,348,187 B1 | 2/2002 | Pan et al. |
| 6,365,130 B1 | 4/2002 | Barry et al. |
| 6,365,209 B2 | 4/2002 | Cherukuri et al. |
| 6,379,652 B1 | 4/2002 | Liu et al. |
| 6,419,903 B1 | 7/2002 | Xu et al. |
| 6,426,085 B1 | 7/2002 | Athanikar |
| 6,444,253 B1 | 9/2002 | Conklin |
| 6,450,935 B1 | 9/2002 | Haworth |
| 6,455,087 B1 | 9/2002 | Nicola |
| 6,464,961 B2 | 10/2002 | Plochocka |
| 6,521,216 B1 | 2/2003 | Glandorf et al. |
| 6,555,094 B1 | 4/2003 | Glandorf et al. |
| 6,576,285 B1 | 6/2003 | Bader et al. |
| 6,579,513 B1 | 6/2003 | Tashjian et al. |
| 6,585,961 B1 | 7/2003 | Stockel |
| 6,592,912 B1 | 7/2003 | Barabolak et al. |
| 6,660,320 B1 | 12/2003 | Pegg et al. |
| 6,741,954 B2 | 5/2004 | Sonnenberg et al. |
| 6,846,498 B2 | 1/2005 | DeAth et al. |
| 6,855,349 B2 | 2/2005 | Greaves et al. |
| 6,858,214 B1 | 2/2005 | Kropf et al. |
| 6,902,738 B2 | 6/2005 | Athanikar et al. |
| 6,921,539 B2 | 7/2005 | Ninkov |
| 6,926,916 B1 | 8/2005 | Day et al. |
| 6,955,827 B2 | 10/2005 | Barabolak et al. |
| 6,996,919 B2 | 2/2006 | Joseph |
| 7,037,543 B2 | 5/2006 | Sandusky et al. |
| 7,083,779 B2 | 8/2006 | Behl et al. |
| 7,087,255 B2 | 8/2006 | McGrew et al. |
| 7,087,552 B2 | 8/2006 | Blowers et al. |
| 7,122,212 B2 | 10/2006 | Kanayama |
| 7,150,876 B2 | 12/2006 | Chaudhuri et al. |
| 7,196,117 B2 | 3/2007 | Beltran et al. |
| 7,247,377 B2 | 7/2007 | Jassan et al. |
| 7,300,675 B2 | 11/2007 | Mori et al. |
| 2001/0046476 A1 | 11/2001 | Plochocka |
| 2002/0025349 A1 | 2/2002 | Brindavanam et al. |
| 2002/0068101 A1 | 6/2002 | DeAth et al. |
| 2002/0081341 A1 | 6/2002 | Sott |
| 2003/0068283 A1 | 4/2003 | Cromwell et al. |
| 2003/0077232 A1 | 4/2003 | Cromwell et al. |
| 2003/0228402 A1 | 12/2003 | Franklin |
| 2004/0013752 A1 | 1/2004 | Wolfson |
| 2004/0067277 A1 | 4/2004 | Barabolak et al. |
| 2004/0081713 A1 | 4/2004 | Maxwell et al. |
| 2004/0161524 A1 | 8/2004 | Sakai et al. |
| 2004/0241186 A1 | 12/2004 | Huang |
| 2004/0253278 A1 | 12/2004 | Maxwell et al. |
| 2004/0254232 A1 | 12/2004 | Beltran et al. |
| 2005/0008732 A1 | 1/2005 | Gebreselassie et al. |
| 2005/0196359 A1 | 9/2005 | D'Amelio, Sr. et al. |
| 2005/0228122 A1 | 10/2005 | Kannan et al. |
| 2006/0013779 A1 | 1/2006 | Dodds et al. |
| 2006/0024351 A1 | 2/2006 | Bradford |
| 2006/0088481 A1 | 4/2006 | Athanikar et al. |
| 2006/0120975 A1 | 6/2006 | Scherl et al. |
| 2006/0134023 A1 | 6/2006 | Pilch et al. |
| 2006/0159818 A1 | 7/2006 | Kunieda |
| 2006/0246016 A1 | 11/2006 | Burzynski |
| 2006/0264347 A1 | 11/2006 | Ming et al. |
| 2006/0275222 A1 | 12/2006 | James Dodds et al. |
| 2007/0031579 A1 | 2/2007 | Draanen et al. |
| 2007/0065394 A1 | 3/2007 | Pinney |
| 2007/0077210 A1 | 4/2007 | Gebreselassie et al. |
| 2007/0077343 A1 | 4/2007 | Ma et al. |
| 2007/0082018 A1 | 4/2007 | Weiss et al. |
| 2007/0166246 A1 | 7/2007 | Takagaki et al. |
| 2007/0221236 A1 | 9/2007 | Kiefer et al. |
| 2008/0058418 A1 | 3/2008 | D'Angelo et al. |
| 2009/0018186 A1 | 1/2009 | Chen et al. |
| 2009/0226549 A1 | 9/2009 | Hughes et al. |

(56) References Cited

U.S. PATENT DOCUMENTS

| | | | |
|---|---|---|---|
| 2010/0034871 | A1 | 2/2010 | Mikkelsen et al. |
| 2011/0059205 | A1 | 3/2011 | Gaysinsky |

FOREIGN PATENT DOCUMENTS

| | | |
|---|---|---|
| DE | 102007057258 | 6/2009 |
| EP | 0304627 | 3/1989 |
| EP | 0497476 | 8/1992 |
| EP | 0605509 B1 | 12/1995 |
| EP | 1336345 | 8/2003 |
| EP | 1280499 | 11/2006 |
| FR | 2632826 | 12/1989 |
| GB | 635053 | 4/1950 |
| GB | 1066391 | 4/1967 |
| GB | 2380407 | 4/2003 |
| RU | 2135552 | 8/1999 |
| RU | 2199330 | 2/2003 |
| WO | WO 92/04884 | 4/1992 |
| WO | WO 97/12607 | 4/1997 |
| WO | WO 97/26855 | 7/1997 |
| WO | WO 98/44926 | 10/1998 |
| WO | WO 99/33352 | 7/1999 |
| WO | WO 99/34773 | 7/1999 |
| WO | WO 00/30467 | 6/2000 |
| WO | WO 01/12144 | 2/2001 |
| WO | WO 01/28649 | 4/2001 |
| WO | WO 01/85099 | 11/2001 |
| WO | WO 03/017962 | 3/2003 |
| WO | WO 03/017963 | 3/2003 |
| WO | WO 03/043593 | 5/2003 |
| WO | WO 2004/019802 | 3/2004 |
| WO | WO 2004/084852 | 10/2004 |
| WO | WO 2005/013712 | 2/2005 |
| WO | WO 2005/070236 | 8/2005 |
| WO | WO 2006/012987 | 2/2006 |
| WO | WO 2006/060145 | 6/2006 |
| WO | WO 2006/125121 | 11/2006 |
| WO | 2008/122286 | 10/2008 |
| WO | WO 2009/105626 | 8/2009 |
| WO | WO 2009/111685 | 9/2009 |
| WO | WO 2011/029077 | 3/2011 |

OTHER PUBLICATIONS

Kleber, C.J. et al., "A mastication device designed for the evaluation of chewing gums," J. Dental Research (1981) 60:109-114.
Rasooli, I. et al., "Rosemarinus officinalis and thymus eriocalyx essential oils combat in vitro and in-vivo dental biofilm formation," Pharmacognosy Magazine (2008) 4(14):65-72.
Sensient, "Templar Technology," 19 pages.
Sensient, "Templar Core Product Portfolio," Edition Two (2006) 4 pages.
Sensient, "Templar Processes" brochure 16 pages.
Sensient, "Templar Key Extraction Processes" brochure 16 pages.
The Engineering Tool: "Ethanol based water solutions," online, http://web.archive.org/web/20060422194844/http://www.engineeringtoolbox.com/ethanol-water-d_989.html, archived to Apr. 2006, 2 pages.
Zasadzlnski, L., "Striving for perfection in flavour enhancement," Innovations in Food Technology (2004) 2 pages.
United States Patent Office Action for U.S. Appl. No. 12/399,295 dated Dec. 7, 2011 (25 pages).
United States Patent Office Action for U.S. Appl. No. 12/399,295 dated Mar. 10, 2011 (16 pages).
International Search Report and Written Opinion for Application No. PCT/US2009/036295 dated Jul. 20, 2009 (9 pages).
Invitation to Pay Additional Fees for Application No. PCT/US2010/047924 dated Jun. 14, 2011 (7 pages).
International Search Report and Written Opinion for Application No. PCT/US2010/047924 dated Sep. 29, 2011 (22 pages).
United States Patent Office Action for U.S. Appl. No. 12/876,124 dated Dec. 3, 2012 (10 pages).
United States Patent Office Final Rejection for U.S. Appl. No. 12/876,124 dated Apr. 8, 2013 (12 pages).
United States Patent Office Final Rejection for U.S. Appl. No. 12/876,124 dated Jan. 9, 2014 (14 pages).
Snyder, Antimicrobial Effects of Spices and Herbs, Hospitality Institute of Technology and Management, St. Paul, Minnesota, Copyright 1997.
United States Patent Office Action for U.S. Appl. No. 14/249,249 dated Sep. 8, 2015 (10 pages).
United States Patent Office Action for U.S. Appl. No. 14/249,249 dated Dec. 7, 2015 (12 pages).
United States Patent Office Action for U.S. Appl. No. 12/876,124 dated Aug. 2, 2013 (15 pages).
United States Patent Office Action for U.S. Appl. No. 14/249,249 dated Apr. 14, 2016 (15 pages).
Segvic et al., "Antifungal activity of thyme (*Thymus vulgaris* L.) essential oil and thymol against moulds from damp dwellings," Letters in Applied Microbiology, 2006, 44(1):36-42.
United States Patent Office Action for U.S. Appl. No. 14/249,249 dated Mar. 29, 2018 (17 pages).
Taherian et al., "Effect of added oil and modified starch on rheological properties, droplet size distribution, opacity and stability of beverage cloud emulsions," Journal of Food Engineering, 2006, 77:687-696.
United States Patent Office Action for U.S. Appl. No. 14/249,249 dated Aug. 29, 2018 (17 pages).
United States Patent Office Action for U.S. Appl. No. 14/249,249 dated Sep. 12, 2019 (22 pages).
Furniss et al., "Vogel's Textbook of Practical Organic Chemistry Fifth Edition," John Wiley & Sons, Inc., New York, 1989, pp. 186-190.
Speight, "Environmental Organic Chemistry for Engineers—Chapter 5: Properties of Organic Compounds," Elsevier: Butterworth-Heinemann, Amsterdam, 2017, pp. 203-261.
United States Patent Office Action for U.S. Appl. No. 14/249,249 dated Oct. 15, 2020 (27 pages).
Zwenger et al., "Plant Terpenoids: Applications and Future Potentials," (2008) University of Northern Colorado School of Biological Sciences Faculty Publications, 4.
Leal et al.,"Functional Properties of Spice Extracts Obtained via Supercritical Fluid Extraction," Journal of Agricultural and Food Chemistry, 2003, vol. 51, Issue 9, pp. 2520-2525.
Shinholt, "Liquid Carbon Dioxide Extraction of Various Food Flavors: Evaluation and Analysis," Butler University Undergraduate Honors Thesis Collection 48. 2009.
United States Patent Office Action for U.S. Appl. No. 14/249,249 dated Nov. 27, 2017 (14 pages).
Chung, "Anticariogenic activity of macelignan isolated from *Myristica fragrans* (nutmeg) against *Streptococcus nutans*," Phytomedicine 13 (2006) 261-266.
United States Patent Office Action for U.S. Appl. No. 14/249,249 dated Oct. 28, 2016 (14 pages).
Oleszek et al., "Saponins in Food, Feedstuffs and Medicinal Plants," Proceedings of the phytochemical society of Europe; copyright 2000 by Springer-Science. (Year: 2000).
Sigma, "Saponin from Quillaja Bark; Product Information Sheet," accessed Mar. 4, 2021 (Year: 2021).
United States Patent Office Action for U.S. Appl. No. 14/249,249 dated Apr. 7, 2021 (22 pages).
United States Patent Office Action for U.S. Appl. No. 14/249,249 dated Aug. 11, 2021 (20 pages).

\* cited by examiner

HERBAL EXTRACTS AND FLAVOR SYSTEMS FOR ORAL PRODUCTS AND METHODS OF MAKING THE SAME

CROSS-REFERENCE TO RELATED APPLICATIONS

This application is a continuation of and claims priority to U.S. application Ser. No. 12/399,295, filed on Mar. 6, 2009, which claims the benefit of U.S. Provisional Application No. 61/034,455, filed Mar. 6, 2008, and U.S. Provisional Application No. 61/034,908 filed Mar. 7, 2008, and U.S. Provisional Application No. 61/034,902, filed Mar. 7, 2008, and U.S. Provisional Application No. 61/073,640, filed Jun. 18, 2008, the entire disclosures of which are incorporated by reference herein.

BACKGROUND

Over the years, many oral products have been developed to include additional ingredients that promote oral hygiene, such as tartar control agents or antibacterial agents, although each of these ingredients brings an added benefit they also cause negative aesthetics, particularly taste. There is still a need for products with improved aesthetics and taste. The present invention provides a method of producing an herbal extract and also a flavor system that can provide both antimicrobial benefits with pleasant organoleptic properties for use in oral products.

SUMMARY

In one aspect, the invention provides a method for preparing an herbal extract including (1) treating an herb with a low temperature liquid $CO_2$ extraction in the presence of an alcohol to produce an alcohol-herb extract; (2) distilling the alcohol-herb extract to remove at least a portion of the alcohol and produce a first herbal extract; and (3) molecularly distilling the first herbal extract to produce a second herbal extract.

In one aspect, the invention provides a flavor system including an herbal extract produced by the above process.

In yet another aspect, the invention provides a flavor system including an herbal extract comprising thymol, eugenol, carvacrol and eucalyptol.

In a further aspect, the invention provides a flavor system comprising a thyme extract having a minimum inhibitory concentration for at least one of *Porphyromonas gingivalis, Actinomycess viscosus, Actinomyces naeslundii, Streptococcus mutans*, and *Fusobacterium nucleatum*, and the minimum inhibitory concentration is less than about 3%.

In another aspect, the invention provides an oral product comprising one of the flavor systems of the present invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The invention provides a process of making an herbal extract. The herbal extract may be derived from thyme, oregano, cilantro, ginger, lavender, allspice, basil, bay, celery seed, pimento, lemongrass, parsley, onion, mustard, tarragon, sage, rosemary, coriander, marjoram, cumin, fennel, cinnamon, clove, black peppercorn and the like. One particularly suitable herbal extract comprises thyme. The herbal extract comprises a mixture of compounds, both active and inactive in providing antimicrobial efficacy and flavor. In a suitable embodiment, the invention provides a process that produces a thyme extract with unique flavoring, coloring, and antimicrobial properties. The process generally includes the following: 1) a first low temperature liquid $CO_2$-alcohol extraction process; 2) a low vacuum distillation process; and 3) a molecular distillation process. The combination of these steps provides a highly concentrated, low color, high flavor and antimicrobial activity herbal extract.

The invention also provides a flavor system for the addition to compositions of oral products such as toothpaste, mouth rinse, gums, lozenges, and the like. The flavor system comprises an herbal extract. The flavor system may also include at least one characterizing flavor component, such as a flavor oil. The flavor system may include a second characterizing flavor component, such as menthol crystals. One suitable embodiment of the flavor system comprises thyme extract, peppermint oil and menthol crystals. The compositions are suitably non-toxic and have antimicrobial activity.

In another aspect, the invention provides a flavor system that provides antimicrobial activity, wherein the antimicrobial activity is measured by a minimum inhibitory concentration. The flavor system comprises an herbal extract, and has a minimum inhibitory concentration that is less than about 3%, less than about 2%, less than about 1%, less than about 0.5%, less than about 0.3%, less than about 0.2%, less than about 0.1%, less than about 0.05% for at least one of *Porphyromonas gingivalis, Actinomyces viscosus, Actinomycess naeslundii, Streptococcus mutans*, and *Fusobacterium nucleatum*.

In yet another aspect, the invention provides an oral composition having antimicrobial activity, the oral composition comprising a flavor system including an herbal extract and at least one characterizing flavor component.

In one aspect, the invention provides a method for producing an herbal extract. The method comprises 1) extracting an alcohol-herbal extract from the herb using a liquid $CO_2$-alcohol extraction at temperatures less than about 25° C.; 2) distilling the alcohol-herbal extract under vacuum to remove at least a portion of the alcohol and produce a first herbal extract; and 3) molecularly distilling the first herbal extract to produce a second herbal extract.

Figure 1:
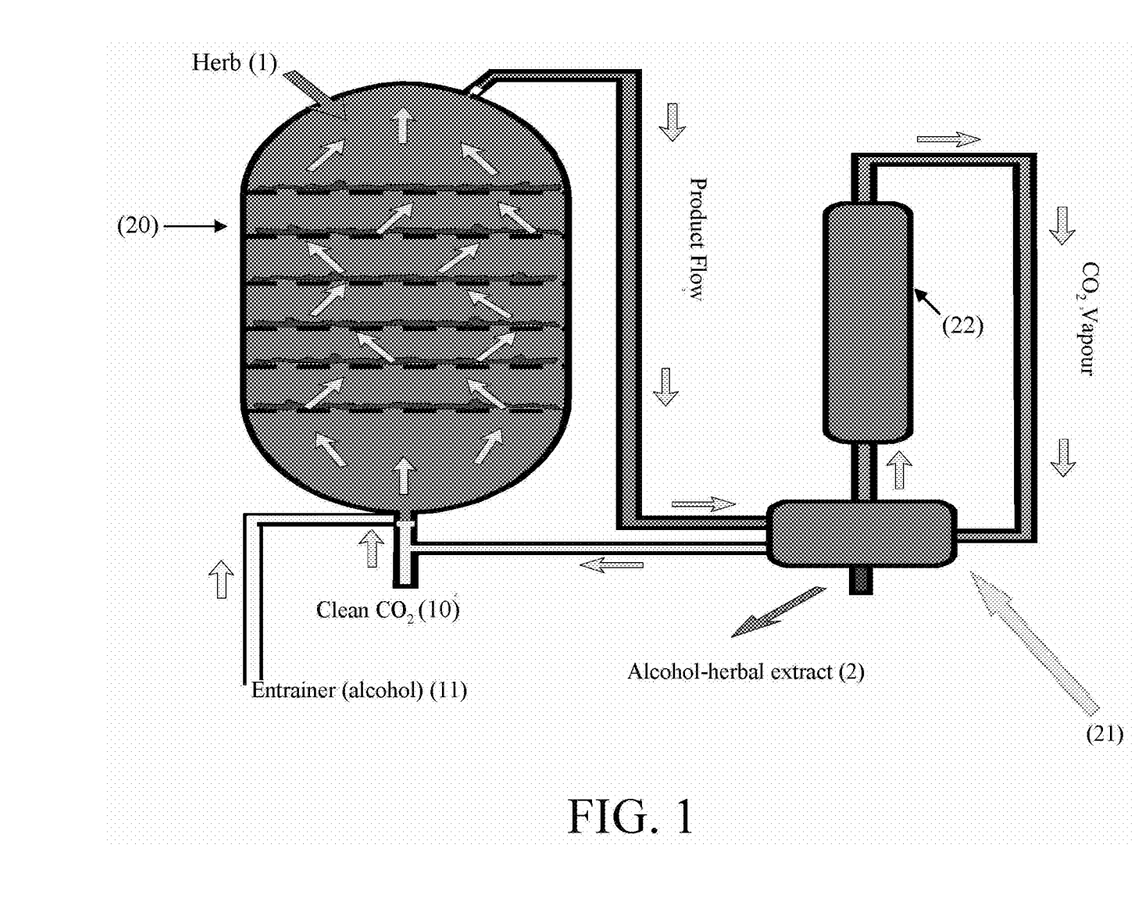
FIG. 1 is a schematic diagram of a system to extract an herbal extract, including treating an herb to a low temperature liquid $CO_2$ extraction process in the presence of ethanol.
Figure 2:
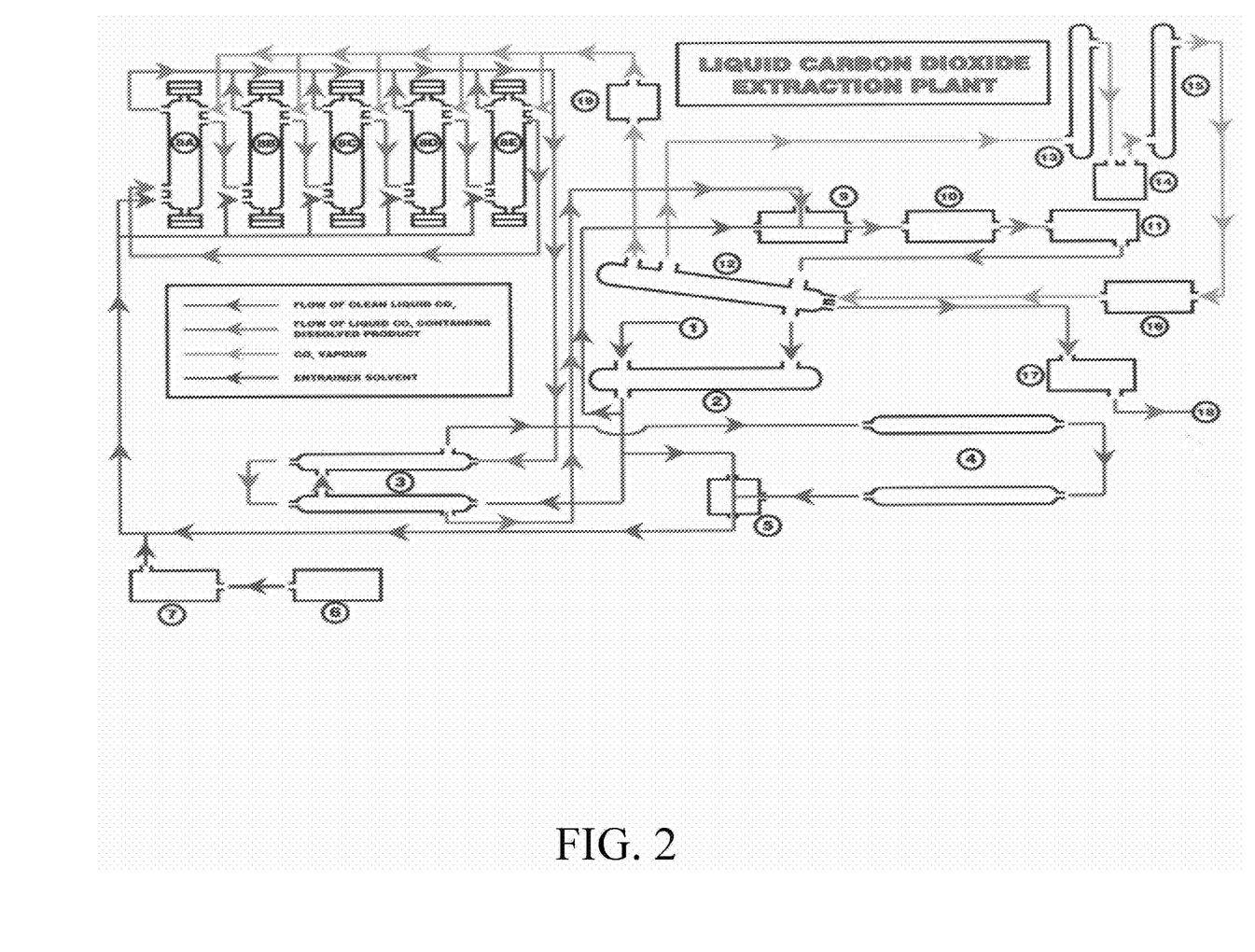
FIG. 2 is a schematic diagram of a liquid $CO_2$-alcohol extraction process.

The first step includes treating the herb to a low temperature liquid $CO_2$ extraction process in the presence of ethanol. This process is illustrated in FIG. 1 and FIG. 2.

Dry herbs (1) are milled on a hammermill with an about 1 millimeter to about 7 millimeter screen to increase the surface area and rupture the herb. The herb is blended with at least about 10%, at least about 15%, at least about 20%, at least about 25%, or at least about 30% of its own weight of de-ionized water, using a ribbon mixer or similar equipment until homogenous, e.g., about 5 minutes. The dampened herb material (1) is packed into a series of extraction columns (20). The columns are treated by dynamic flow of liquid carbon dioxide (10) injected with alcohol (11) as a co-extraction entrainer. In a suitable embodiment, the amount of $CO_2$-alcohol used can be measured as a mean flow rate through the extraction column. Suitable flow rates include at least about 150 kg/hr, at least about 175 kg/hr, at least about 200 kg/hr, at least about 222 kg/hr, or at least about 240 kg/hr. The flow rate may be less than about 350 kg/hr, less than about 325 kg/hr, less than about 300 kg/hr, less than about 275 kg/hr, or less than about 260 kg/hr.

The ratio of $CO_2$ to alcohol may vary according to the herb being processed. In a suitable embodiment, the alcohol is provided in at least about 0.1%, at least about 0.2%, at least about 0.3%, at least about 0.5%, at least about 0.7%, at least about 1.0%, or at least about 2.0% by weight in the liquid $CO_2$. In a suitable embodiment, the alcohol is provided at a mean flow rate of 1 kg/hr with the $CO_2$ provided at a mean flow rate of 250 kg/hr. In one embodiment, the alcohol is ethanol.

The $CO_2$-alcohol is provided to the extraction columns under pressure, the pressure being at least about 35 atmosphere, at least about 40 atmosphere, at least about 45 atmosphere, at least about 50 atmosphere, at least about 55 atmosphere, or at least about 60 atmosphere, wherein a suitable range is about 45-55 atmosphere. The process is driven by an approximately 10 atmosphere differential within the plant during operation.

In certain embodiments, this process is carried out at temperatures that are less than about 25° C., less than about 20° C., less than about 15° C., less than about 12° C. Suitably the temperature may be between about 0° C. and about 10° C. In a suitable embodiment, the temperature is about 7° C.±1° C. These temperatures are below the temperatures used in supercritical $CO_2$ extraction which occur above the critical temperature 31° C., and more typically at 40-60° C., and very often higher. The lower temperatures concentrate more of the volatile components in the extract and avoid the decomposition of components. The liquid $CO_2$ phase extraction is more selective for more volatile components and therefore achieves higher concentrations of them.

The liquefied carbon dioxide-alcohol is a unique solvent mixture that dissolves the low molecular weight organoleptically active components of the herb. The low temperature and pressurized system prevents the degradation and loss of volatiles which may typically occur with a traditional essential oil distillation process, while higher molecular weight unwanted materials such as heavier fats, waxes, pigments, sugars, starches and tannins are excluded by this extraction process. The $CO_2$-alcohol-herb extract solution emerging from the extraction columns is passed to a heat exchanger (21) where the temperature is raised a few degrees within the closed system, and the $CO_2$ is changed to vapor by the change in temperature and removed via pipe work to the compressor for recycling to liquid $CO_2$ through the process. The alcohol-extract is collected from the system as a cold foam product, and as the foam warms to room temperature any residual $CO_2$ vaporizes and leaves the alcohol-herbal extract (2). The time of extraction depends on the material used and can be readily determined by one of ordinary skill in the art. For a thyme extract, the extraction time per extraction column filled with thyme leaves (about at least 25 kg, more suitably 28 kg) is at least about 4 hours.

FIG. 2 charts a description of the $CO_2$-alcohol extraction process in detail. Liquid $CO_2$ 1 enters the system into a liquid $CO_2$ holding tank 2. The $CO_2$ is processed through a heat exchanger 3 and a refrigeration unit 4 to provide the liquid $CO_2$ at the desired temperature of about 7° C. The liquid $CO_2$ is injected with alcohol from an alcohol storage tank 6 via a co-entainer pump 7. The liquid $CO_2$-alcohol solvent is pumped through a set of extraction columns 8A-E which hold the milled herbal leaves. The liquid $CO_2$-alcohol-herbal extract is processed through the heat exchanger 3 (giving an initial input of energy into the extract) to an automatic mixing valve 9, an automatic flow control valve 10 and filters 11 into a main condenser-heat exchanger 12 where the $CO_2$ is recycled back into the $CO_2$ holding tank 2 and the product is collected via the product collection pump 17 to a product tap 18. $CO_2$ is also purified to be reused and recovered from the condenser-heat exchanger 12 through a demisting filter 13, a compressor 14, a de-oil misting filter 15 and at a vapor temperature control 16. A vaporizer 19 pumps warm vapor back into the extraction columns 8.

Figure 3:
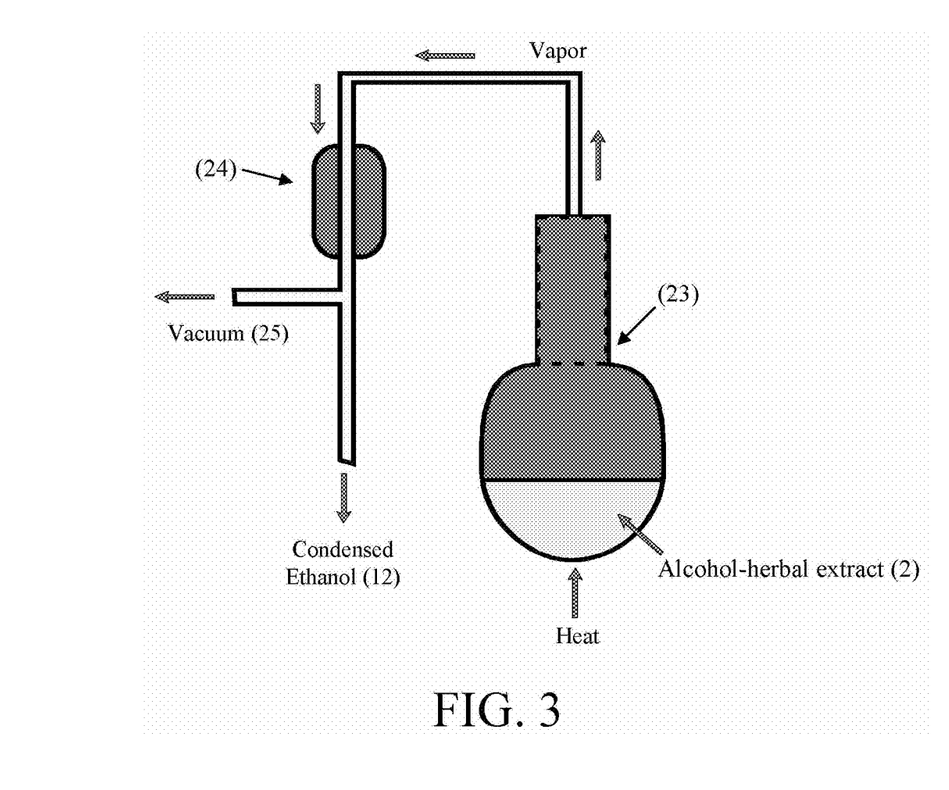
FIG. 3 is a schematic diagram of a process to remove alcohol from an alcohol-herbal extract resulting from a liquid $CO_2$-alcohol extraction process, using low vacuum distillation.

A second step of the process includes processing the alcohol-herbal extract from the extraction through a low vacuum distillation process to remove the alcohol as depicted in FIG. 3 and form a first herbal extract (3). This process can be carried out using a suitable vacuum still (23). The alcohol is removed under low vacuum distillation at typically a temperature of at least about 20° C., at least about 30° C., at least about 35° C., at least about 40° C., at least about 45° C., at least about 50° C., at least about 55° C., or at least about 60° C., one suitable range is between about 30 to about 40° C., finishing at a maximum of about at least 60° C., to reduce the alcohol content to a residual level. Residual alcohol may be less than about 25%, less than about 20%, less than about 15%, or less than about 10%. The residual alcohol may be at least about 0.05%, at least about 0.1%, at least about 0.2%, at least about 0.5%, at least about 1%, at least about 2%, or at least about 5%.

Figure 4:
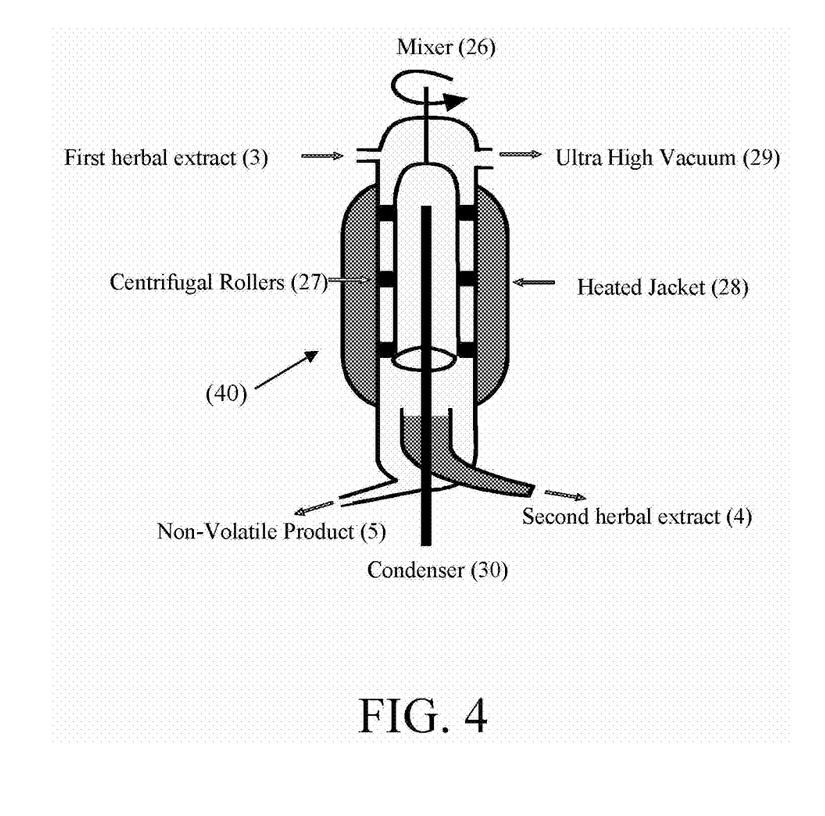
FIG. 4 is a schematic diagram of a molecular distillation process to produce a final herbal extract that is a concentrated distillate.

A third step of the process includes a molecular distillation process. A falling-film short path still may be used. Suitable stills such as models KD5 or KD10 Molecular Stills are available from UIC GmbH of Germany. This step of the process is depicted in FIG. 4. This special design of the still subjects the material being processed to heating for the briefest possible time while allowing a very high vacuum to be achieved, lowering the vaporizing temperature and thus greatly limiting the overall exposure of the extract. Suitably, the liquid extract (3) is continuously feed into the still (40) and passes down the inside of a heated jacket (28), which is at about at least 80° C., at least about 90° C., or at least about 100° C., as a thin film produced by the centrifugal force of the rotating rollers (27), and falls by gravity to be collected. This process is carried out under high vacuum conditions, wherein the pressure is suitably at least about $5 \times 10^{-4}$ mbar, at least about $1 \times 10^{-3}$ mbar, at least about $1.5 \times 10^{-3}$ mbar, or at least about $2 \times 10^{-3}$ mbar. The pressure is suitably at least less than about $1 \times 10^{-2}$ mbar, less than about $5 \times 10^{-2}$ mbar, less than about $7 \times 10^{-2}$ mbar, or less than about $1 \times 10^{-3}$. The extract is subjected to heat typically for only a few minutes. Suitably, the extract passes through the system at a rate of about at least 1 kg/hr, at least about 2 kg/hr, at least about 3 kg/hr, at least about 5 kg/hr, at least about 7 kg/hr, at least about 8 kg/hr, or at least about 10 kg/hr. In a suitable embodiment, the rate is about 1 to about 2 kg/hr for a KD10 Molecular Still. The volatile material passes as a laminar flow of vapor across a very short path onto a condenser (30) which is concentric at the center of the roller assembly, and falls by gravity into a receiver. This laminar flow, coupled with the use of high efficiency rotary and oil diffusion vacuum pumps and a liquid nitrogen trap at −200° C. allows vacuum pressures down to $10^{-6}$ atmosphere to be achieved. Materials in the extract that would be damaged or even decomposed during traditional distillation are separated and purified into the final herbal extract. This process produces a second herbal extract (4) that is a concentrated distillate with reduced color.

As mentioned above, the invention also provides a flavor system comprising the herbal extract. The herbal extract is suitably provided as at least about 1% wt/wt, at least about 2% wt/wt, at least about 4% wt/wt, at least about 6% wt/wt, at least about 9% wt/wt, at least about 15% wt/wt, at least about 20% wt/wt, or at least about 25% wt/wt of the flavor system. The thyme extract is suitably provided as less than about 30% wt/wt, less than about 20% wt/wt, less than about 15% wt/wt, less than about 12% wt/wt of the flavor system.

One suitable herbal extract is a thyme extract derived from dry thyme by the process described above. The thyme extract is a mixture of compounds, both active and inactive in providing antimicrobial efficacy and flavor. Suitable processes produce thyme extract with unique flavoring and antimicrobial properties. This thyme extract has unique and beneficial properties from thyme oils produced by other known methods. The main active ingredients of the thyme extract that provide antimicrobial efficacy include thymol, eugenol, carvacrol and eucalyptol. Thyme extract also includes a number of inactive ingredients, some of which can be found in Table 7. The unique chemical composition of this extract provides the unique flavor, color and antimicrobial properties. The thyme extract provides a more appealing flavor in addition to antimicrobial benefits. One example of a suitable thyme extract is THYME TEMPLAR™ available from Sensient Flavors, Inc. (Indianapolis, Ind.).

The flavor system may also include at least one characterizing flavor component that provides organoleptic properties of pleasant taste and smell, and may provide additional antimicrobial activity as well. A first characterizing flavor component may constitute suitably at least about 5%, at least about 10%, at least about 20%, at least about 30%, at least about 47%, at least about 50%, at least about 60%, or at least about 70% wt/wt of the flavor system. The first characterizing flavor component may constitute less than about 70% wt/wt, less than about 60% wt/wt, less than about 55% wt/wt, less than about 50% wt/wt, less than about 40% wt/wt, or less than about 20% wt/wt of the flavor system. The first characterizing flavor component may be a flavor oil. Examples of flavor oils that may be used include, but are not limited to, peppermint oil, spearmint oil, oil of wintergreen, lavender oil, rosemary oil, clove oil and cinnamon oil.

The flavor system may also include a second characterizing flavor component. The flavor system may suitably includes at least about 5%, at least about 10%, at least about 20%, at least about 30%, at least about 40%, at least about 50% wt/wt, at least about 60% wt/wt, or at least about 70% wt/wt of the secondary flavor component. The flavor system may suitably include less than about 70%, less than about 60%, less than about 50%, less than about 40%, less than about 30%, less than about 20%, less than about 15%, or less than about 10% of the secondary flavor component. One example of a secondary flavor component includes, but is not limited to, menthol crystals, $C_{10}H_{20}O$, which are an organic compound made synthetically or obtained from mint oils, most commonly produced from *Mentha arvensis*. Menthol is a waxy, clear or white crystalline substance commercially available from Monarchy Aromatics, Ltd.

Additional examples of first and second characterizing flavor components may be from oils, crystals, liquid concentrates, synthetic flavors, or combinations thereof. Additional characterizing flavor components may include, but are not limited to, oils derived from plants and fruit such as citrus oils, fruit essences, peppermint oil, spearmint oil, other mint oils, clove oil, oil of wintergreen, cinnamon, anise, artificial flavoring agents such aldehyde flavors including, but are not limited to, acetaldehyde (apple), benzaldehyde (cherry, almond), anisic aldehyde (licorice, anise), cinnamic aldehyde (cinnamon), citral, i.e., alpha citral (lemon, lime), neral, i.e., beta citral (lemon, lime), decanal (orange, lemon), ethyl vanillin (vanilla, cream), heliotropine, i.e., piperonal (vanilla, cream), vanillin (vanilla, cream), alpha-amyl cinnamaldehyde (spicy fruity flavors), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., Melonal (melon), 2,6-dimethyloctanal (green fruit), and, 2-dodecenal (citrus, mandarin). Those skilled in the art will recognize that natural and artificial secondary flavor components may be combined in any sensorally acceptable fashion. All such flavors and flavor blends are contemplated by the present invention.

As mentioned above, the invention also provides a flavor system comprising an herbal extract. "Antimicrobial activity," as described herein, is the ability of an herbal extract to retard the growth of and/or prevent the growth of oral bacteria. Examples of representative gram-positive and gram-negative oral bacteria include, but are not limited to, *Actinmoyces viscosus Actinomyces naeslundii, Fusobacteriumm nucleatum, Porphyromonas gingivalis, Streptococcus mutans*, and *Streptococcus sanguis*. Anti-microbial activity can be measured by the minimum inhibitory concentration of the agent. The minimum inhibitory concentration of an herbal extract is the concentration of the extract within a test sample at which no bacterial growth is observed. The test sample may be saliva or a suitable bacterial culture. In the examples below, the minimum inhibitory concentration is provided as a percentage.

The minimum inhibitory concentration for the herbal extract is measured as a percent volume (e.g., 1% would be one part flavor system in 99 parts test sample) as described in the example below. The herbal extract may provide antimicrobial activity as measured by minimum inhibitory concentration (MIC) of at least about 0.01%, at least about 0.05%, at least about 0.1%, at least about 0.2%, at least about 0.5% for an oral bacteria. The herbal extract may provide antimicrobial activity as measured by minimum inhibitory concentration of less than about 5%, less than about 3%, less than about 2%, less than about 1%, less than about 0.5%, less than about 0.3%, less than about 0.2%, less than about 0.1% for an oral bacterial.

The flavor system may include additional antimicrobial agents. Suitable antimicrobial agents include, but are not limited to, cedarwood oil, chloramphenicol, berberine, *Glycyrrhiza glabra* extract, juicy fruit basil oil, juniper berries oil, lemon basil oil, orally active metallic ion such as salts of zinc, tin, silver and copper, hexylresorcinol, cetylpyridinium chloride, chlorhexidine digluconate, 5-chloro-2-(2,4-dichlorophenoxy)-phenol, commonly referred to as triclosan, phthalic acid and its salts including, but not limited to those disclosed in U.S. Pat. No. 4,994,262, substituted monoperthalic acid and its salts and esters as disclosed in U.S. Pat. Nos. 4,990,329, 5,110,583, and 4,716,035, magnesium monoperoxy phthalate, chlorhexidine (Merck Index, no. 2090), alexidine (Merck Index, no. 222, hexetidine (Merck Index, no. 4624), sanguinarine (Merck Index, no. 8320), benzalkonium chloride (Merck Index, no. 1066), salicylanilide (Merck Index, no. 8299), domiphen bromide (Merck Index, no. 3411), cetylpyridinium chloride (CPC) (Merck Index no. 2024, tetradecylpyridinium chloride (TPC), N-tetradecyl-4-ethyllpyridinium chloride (TDEPC), octenidine, delmopinol, octapinol, and other piperidino derivatives, niacin preparations, zinc/stannous ion agents, antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above. Each of the patents recited herein are hereby fully incorporated by reference.

Sweeteners may also be included in the flavor system. Suitable sugar sweeteners include, but are not limited to, sucrose, dextrose, maltose, dextrin, dried invert sugar, fructose, glucose, galactose, corn syrup solids, stevioside, Lo-Han Guo, and the like, alone or in combination. Sugarless sweeteners include, but are not limited to, sugar alcohols such as sorbitol, mannitol, xylitol, hydrogenated starch hydrolysates, maltitose, and the like, alone or in combination. High intensity artificial sweeteners can also be used alone or in combination with other sweeteners. These sweeteners include, but are not limited to, sucralose, aspartame, MAPM derivatives such as neotame, salts of acesulfame, altitame, saccharin and its salts, cyclamic acid and its salts, glycyrrhizinate, dihydrochalcones, thaumatin, monellin, and the like, alone or in combination.

In one embodiment, the flavor systems are manufactured by mixing a first characterizing flavor component (e.g., peppermint oil) with a second characterizing flavor component (e.g., menthol crystals) and heating the mixture to at least about 35° C., to at least about 40° C., to at least about 45° C., to at least about 50° C., to at least about 55° C., to at least about 60° C., to at least about 65° C. until the second characterizing flavor component is melted in a standard mixer. The mixture is mixed until homogeneous and then cooled. The thyme extract is added to the mixture and mixed until homogeneous. In another embodiment, the thyme extract may be added to a first characterizing flavor component without the use of a second flavoring component and mixed until homogeneous. The thyme extract and first characterizing flavor component may be mixed at room temperature. Other flavors may also be added and mixed until homogeneous.

The flavor systems may be used in the preparation of spray dried flavor compositions. The flavor systems may be combined with encapsulating agents such as the starch-based encapsulating agent Hi-Cap 100 from National Starch (Bridgewater, N.J., U.S.A.) and water. Other suitable encapsulating agents may include N-Lok® 1930, CAPSUL®, CAPSUL®TA (all from National Starch), and EmCap™ (from Cargill, Inc., Cedar Rapids, Iowa, U.S.A.). The water and starch-based encapsulating agent may be mixed, and a flavor system may be added to the starch and water mixture to form an emulsion. The emulsion may be dried with an inlet temperature of about 160° C. The encapsulating agent may be present in amounts of at least about 5%, at least about 10%, at least about 20%, at least about 30%, at least about 40%, or at least about 50% by weight of the total spray dried flavor composition. The encapsulating agent may be present in a suitable amount less than about 50%, less than about 40%, less than about 20%, less than about 10%, or less than about 5% by weight of spray dried flavor composition. The flavor system may be added to amounts of at least about 0.5%, at least about 0.8%, at least about 1%, at least about 2%, at least about 4%, at least about 6%, at least about 10%, at least about 20%, at least about 30%, at least about 40%, at least about 50%, at least about 60%, or at least about 70% by weight of the total spray dried flavor composition. The flavor system may be used in the composition in a suitable amount less than about 60%, less than about 50%, less than about 20%, less than about 12%, less than about 10%, less than about 7%, less than about 5%, less than about 3%, or less than about 2% by weight of spray dried flavor composition. The spray dried flavor formulations may be used with or without other flavor systems and may be incorporated into compositions such as water, chewing gums, toothpaste, mouth rinse, liquid dentifrice, lozenges, liquid spray, and edible films.

The flavor systems may be used in the preparation of oral compositions for oral products by the addition of the flavor system at amounts of at least about 0.5%, at least about 0.8%, at least about 1%, at least about 2%, at least about 4%, at least about 6%, at least about 10% by weight of the total oral composition. The flavor system may be used in the oral composition in a suitable amount less than about 20%, less than about 12%, less than about 10%, less than about 7%, less than about 5%, less than about 3%, less than about 2% by weight of the oral composition. Oral compositions may be products which in the ordinary course of usage are not intentionally swallowed for purposes of systemic administration of particular therapeutics agents, but are rather retained in the oral cavity for a time sufficient to contact substantially all the dental surfaces and/or oral tissues for purposes of oral activity. Methods of preparing the oral compositions may include mixing the flavor system by conventional methods to an oral delivery agent. Oral delivery agents include, but are not limited to, a toothpaste, mouth rinse, liquid dentifrice, gum, lozenges, liquid spray, and edible films. Toothpaste may be paste or gel formulations unless otherwise specified. The amount of flavor system added depends on the particular oral composition to which it is added. For example, chewing gums may include at least about 0.5%, more suitably at least about 2% wt/wt of flavor system while edible oral films may comprise at least about 6%, more suitable at least about 10% wt/wt of the flavor system due to their very low weight. The oral compositions comprise a sufficient amount of the flavor system to provide antimicrobial activity.

The oral compositions may include sweeteners as described above. Further, the oral compositions may include other antimicrobial agents. The oral compositions may also contain other flavoring agents, if desired. The flavoring agents may include essential oils, synthetic flavors or mixtures thereof including, but not limited to, oils derived from plants and fruits, such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorally acceptable fashion. Flavoring may include a cooling agent to enhance the flavor and perceived freshness.

The oral compositions may be chewing gums or any variation including but not limited to bubble gums, pellets, gum balls or sticks. Chewing gums may be coated or not coated and be of a variety of flavors, shapes and sizes. A chewing gum composition includes a gum base, and a suitable amount of the flavor system as described above. Chewing gum may be manufactured by any suitable conventional method. The base for the chewing gum includes an elastomer of a type normally employed in chewing gums, e.g., chicle, gum, jelutong, balata, crown gum, gutta-percha, sorva, butadiene-styrene copolymer, polyisobutylene, isobutylene-isoprene copolymer, polyethylene, and the like or mixtures thereof. Softeners may be added to chewing gum in order to optimize the chewability and mouth-feel of the gum. Chewing gums may include at least about 0.1%, at least about 0.5%, at least about 1%, at least about 2% of the flavor system. Chewing gums may include less than about 3%, less than about 2.5%, less than about 2% of the flavor system.

The following examples further describe and demonstrate embodiments within the scope of the present invention. These examples are given solely for the purpose of illustration and are not to be construed as limitations of the present invention as many variations thereof are possible without departing from the spirit and scope.

EXAMPLES

All percentages described in the following examples are percent weight unless indicated otherwise.

Example 1

Dry thyme leaves were milled on a hammermill with a 3 millimeter screen to increase the surface area and rupture the leaves. 28 kg of dry milled thyme leaves were added to 8.4 kg of water and mixed in a ribbon mixer until homogenous, about 5 minutes. The moistened thyme leaves were added to a stainless steel extraction column. Each extraction column was loaded with 28 kg dry thyme leaves. Three extraction columns were used. Liquid $CO_2$ was injected with 1 kg/hr of ethanol (96 A % natural fermentation grade), the $CO_2$ provided to the extractor at a rate of 250 kg/hr for 4 hours per extraction column under 45 atmosphere pressure at 7° C.±1°. The $CO_2$-ethanol-thyme extract was collected and passed through a heat exchanger which vaporizes the $CO_2$ to produce an ethanol-thyme extract to yield about 17% the weight of the initial leaves at this stage. The ethanol-thyme extract was processed by low vacuum distillation at 35° C. at 200 mbar to remove the ethanol in a batch still. The distilled thyme-extract was then treated on a thin-film molecular distillation unit (KD5 model, UIC GmbH of Germany) under vacuum pressure of $10^{-6}$ atmospheres at 100° C. at a flow rate of 1 kg per hour. The thyme extract was analyzed by mass spectroscopy and an exemplary list of the chemical composition of the thyme extract is shown in Table 1.

TABLE 1

| Thyme extract | |
|---|---|
| Compound | % |
| Ethanol | 5.03 |
| Acetic Acid | 0.349 |
| 1-octen-3-ol | 1.031 |
| p-cymene | 6.382 |
| Eucalyptol | 0.43 |
| Linalool | 2.354 |
| Camphor | 0.232 |
| Boreol | 1.423 |
| 4-terpineol | 0.542 |
| thymol methyl ether | 0.701 |
| carvacrol methyl ether | 1.141 |
| Thymol | 58.468 |
| Carvacrol | 4.436 |
| Eugenol | 0.589 |
| beta-caryophyllene | 1.326 |
| caryophyllene oxide | 0.794 |
| Total | 85.228 |

Example 2

A flavor system was formulated using the components set forth in Table 2.

TABLE 2

| Flavor B | % material in formula | % material in final flavor system |
|---|---|---|
| Thyme extract (THYME TEMPLAR™, Sensient Flavors, Indianapolis, IN) | | 1-12% |
| Primarily composed of: | | |
| Thymol | 1-50% | |
| Eugenol | 0.01-5% | |
| Carvacrol | 0.1-10% | |
| Eucalyptol | | |
| Menthol crystals (Monarchy Aromatics, Ltd,) | | 15-50% |
| Peppermint oil (F. D. Copeland and Sons, Ltd) | | 25-60% |
| Natural Thymol | | 0.1-0.8% |
| TOTAL | | 100% |

The peppermint oil and menthol crystals were added together in a standard mixer and heated to 113° F. and mixed until homogenous. The mixture was then cooled and the thyme extract and natural thymol were added and mixed until homogenous.

Example 3

A flavor system formulation was prepared using the following formulation in Table 3.

TABLE 3

| Flavor C | % material in formula | % material in final flavor system |
|---|---|---|
| Thyme extract (THYME TEMPLAR ™, Sensient Flavors, Indianapolis, IN) Primarily composed of: Thymol Eugenol Carvacrol Eucalyptol | 50% 7% | 5% (2.5-3%) |
| Menthol crystals (Monarchy Aromatics, Ltd,) | | 40% |
| Peppermint oil (F. D. Copeland and Sons, Ltd) | | 55% |
| TOTAL | | 100% |

The peppermint oil and menthol crystals were added together in a standard mixer, heated to 113° F. until the menthol crystals dissolved, and the mixture was cooled. The thyme extract was then added to the mixture and mixed until homogeneous.

A batch of flavor system formulation C was analyzed by gas chromatography/mass \spectrometry (GC/MS) using standard methods providing the main chemical composition of formulation C as shown in Table 4.

TABLE 4

Flavor C composition

| Compound | % |
|---|---|
| b-cymene | 0.376 |
| Eucalypto + Limonene | 2.892 |
| Menthone | 13.125 |
| Isomenthone | 2.798 |
| Menthofuran | 1.609 |
| Neomenthol | 2.317 |
| Menthol | 63.53 |
| Pulegone | 1.059 |
| Thymol | 2.506 |
| Methyl Acetate | 2.578 |
| Beta- caryophyllene | 1.038 |
| Germacrene | 0.416 |
| Other ingredients | 5.8 |
| Total | 100 |

Example 4

A flavor system formulation was prepared as described in Example 3 but using the following formulation in Table 5.

TABLE 5

| Flavor D | % material in formula | % material in final flavor system |
|---|---|---|
| Thyme Templar (THYME TEMPLAR ™, Sensient Flavors, Indianapolis, IN) Primarily composed of: Thymol Eugenol Carvacrol Eucalyptol | 50% 7% | 9% (2.5-3%) |
| Menthol crystals (Monarchy Aromatics, Ltd,) | | 38% |
| Peppermint oil (F. D. Copeland and Sons, Ltd) | | 53% |
| TOTAL | | 100% |

A batch of flavor system of formulation D was analyzed as described in Example 3. The formulation of the main chemical compositions of formula D can be found in Table 6.

TABLE 6

Flavor D composition

| Compound | % |
|---|---|
| b-cymene | 0.638 |
| eucalypto + Limonene | 2.623 |
| Menthone | 11.805 |
| Isomenthone | 2.53 |
| Menthofuran | 1.445 |
| Neomenthol | 2.122 |
| Menthol | 62.895 |
| Pulegone | 1 |
| Thymol | 4.963 |
| Methyl Acetate | 2.514 |
| Beta- caryophyllene | 0.97 |
| Germacrene | 0.379 |
| Other | 6.116 |
| Total | 100 |

Example 5

Chewing Gum Containing Flavor Systems

Chewing gum compositions are prepared by incorporating the flavor systems of Examples 3 and 4 with a chewing gum (Trident gum manufactured by Cadbury Adams located in Parsippany N.J.). The flavor systems are added at 2% weight of the composition of the gum.

Example 6

Liquid Filled Chewing Gum

Liquid filled chewing gum compositions, Dentyne Ice (manufactured Cadbury Adams located in Parsippany N.J.), are prepared by incorporating the flavor systems of Examples 3 and 4, the liquid portion of Dentyne Ice gum filling is mixed with 0.1% of the flavor system and the solid portion of the Dentyne Ice gum base is mixed with 3% of the flavor system.

Example 7

Liquid Filled Chewing Gum

Liquid filled chewing gum compositions, Dentyne Ice (manufactured by Cadbury Adams located in Parsippany N.J.), are prepared by incorporating the flavor systems of Examples 3 and 4, the liquid portion of Dentyne Ice gum filling is mixed with 1.0% of the flavor system and the solid portion of the Dentyne Ice gum base is mixed with 3% of the flavor system.

Example 8

Mouth Rinse Containing Flavor System

Mouth rinse compositions are prepared by mixing 2% by weight of the flavor systems of Examples 3 and 4 with a mouth rinse.

Example 9

Toothpaste Containing Flavor System

Toothpaste compositions are prepared by mixing 2% of flavor systems of Examples 3 and 4 with unflavored toothpaste until the mixture is homogenous.

Example 10

Edible Film Containing Flavor System

Edible film compositions are prepared by mixing 10% by weight of the flavor systems of Examples 3 and 4 with a substance to form an edible film.

Example 11

Composition of Thyme Extract

The composition of the thyme extract (THYME TEMPLAR™) obtained by ethanol $CO_2$ extraction process was analyzed as described in Example 3. An exemplary list of the chemical composition is shown in Table 7.

TABLE 7

| Thyme extract | |
|---|---|
| Compound | % |
| Ethanol | 5.03 |
| Acetic Acid | 0.349 |
| 1-octen-3-ol | 1.031 |
| p-cymene | 6.382 |
| Eucalyptol | 0.43 |
| Linalool | 2.354 |
| Camphor | 0.232 |
| Boreol | 1.423 |
| 4-terpineol | 0.542 |
| thymol methyl ether | 0.701 |
| carvacrol methyl ether | 1.141 |
| Thymol | 58.468 |
| Carvacrol | 4.436 |
| Eugenol | 0.589 |
| beta-caryophyllene | 1.326 |
| caryophyllene oxide | 0.794 |
| Total | 85.228 |

Example 12

Antimicrobial Activity of Flavor System

In vitro studies were preformed at Indiana University School of Dentistry at the Indiana University-Purdue University of Indianapolis (IUPUI) to test for the antimicrobial activity of the flavor systems. *Porphyromonas gingivalis* (PG, ATCC 33277), *Actinomyces viscosus* (AV, ATCC 19246), *Actinomycess naeslundii* (AN, ATCC 12104), *Streptococcus mutans* (SM, ATCC 25175), and *Fusobacterium nucleatum* (FN, ATCC 31647) were used to determine the minimum inhibitory concentration of 4 different flavor systems, A-D. Thyme extract is Flavor A as described in Example 8, and flavor systems B-D are as described in Examples 2-4. The four flavor systems were provided in an undiluted form and each flavor system was diluted to the working test solutions of 1.0%, 0.5%, 0.05%, and 0.001% (v/v) flavor system. Each testing system had a final volume of 2.0 ml, each containing at least $1 \times 10^6$ bacteria, adequate amount of the flavor system to obtain the working test solution, 1 ml of double strength enriched trypticase-soy broth and saline solution to bring the final volume up to 2 ml. Each test was run in triplicate.

Each testing sample was vigorously vortexed for 30 to 60 seconds to enhance physical contact of the bacteria with the relatively insoluble test products. A 1.0 ml aliquot was taken and placed into a flask containing 250 ml of Trypticase Soy Broth (TSB) supplemented with 0.25% (w/v) glucose. Flasks containing *Porphyromonas gingivalis* or *Fusobacterium nucleatum* were incubated at 37° C. in an anaerobic chamber (85% $N_2$-10% $CO_2$-5% $H_2$), while the other bacteria flasks were incubated at 37° C. in ambient air. Samples were evaluated after 24 hours. The minimal inhibitory concentration (MIC) was determined as the test sample with the greatest dilution that exhibited no bacteria growth (e.g., remained clear, not turbid). MIC scores for each of the flavor systems for each of the bacteria tested are shown in Table 8.

TABLE 8

| Flavor | FN | AN | AV | PG | SM |
|---|---|---|---|---|---|
| A | 0.05% | 0.05% | 0.05% | <0.01% | 0.05% |
| B | 0.05% | 0.1% | 0.5% | 0.05% | 0.5% |
| C | 0.05% | 0.5% | 0.1% | 0.05% | 0.1% |
| D | 0.1% | 0.1% | 0.5% | 0.05% | 1% |

Example 13

Flavor Release from Chewing Gum

To test if adequate flavor is released from chewing gum, the chewing gums made in Example 5 were tested using a mechanical instrument to simulate human mastication of chewing gum, which can be found in Kleber et al. A mastication device designed for the evaluation of chewing gum is set forth in Journal of Dental Research, 1981, 109-114, which is incorporated herein in its entirety. Artificial saliva (15 ml) was placed in the reservoir, and the thermostatically controlled heating element was turned on to maintain the saliva and gum at body temperature for proper chewing consistency. One stick of test chewing gum (approximately 3 grams with 2% flavor system added) was placed in the warmed chamber and the artificial saliva was exposed to the chewing gum for 1 minute under chewing simulation conditions. All the artificial saliva (15 ml) was removed as quickly as possible with a pipette, delivered immediately into a glass bottle and sealed. The saliva was replaced with a fresh 15 ml aliquot, the chewing conditions restarted and the gum samples were treated for another minute. This process was repeated at the appropriate intervals to yield cumulative treatment times of 1, 2, 5, 10, 15, 20 and 30 minutes. The reservoir and mastication devices were thoroughly cleaned and rinsed, and the process repeated with another sample of chewing gum.

Figure 5:
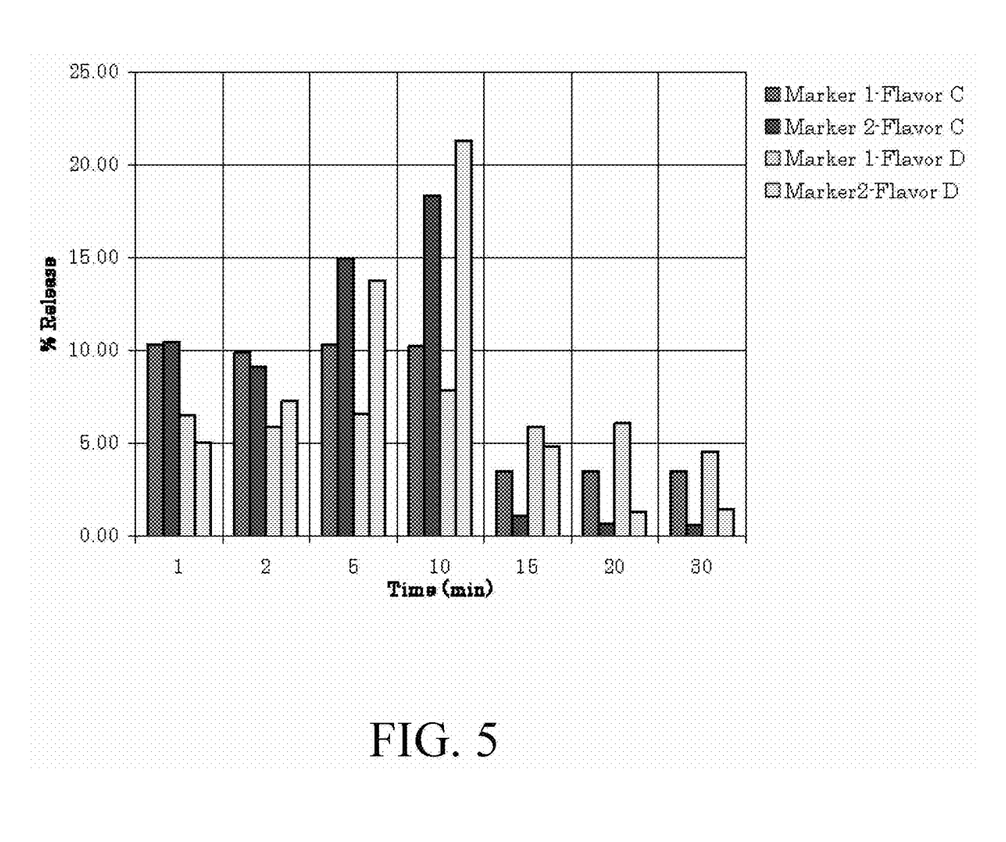
FIG. 5 is a graph of percent release of Marker 1, thymol, and Marker 2, menthol, from chewing gum versus time, to monitor flavor release.

Two markers, Marker 1, thymol, and Marker 2, menthol, were selected to monitor flavor release based on quantity and antimicrobial efficiency. FIG. 5 shows release of the two markers at different predetermined times. Based on marker release, it was estimated that most of the flavor was released for Marker 2 between 5 and 10 minutes of chewing. Marker 1 was released constantly for the first 10 minutes and afterward decreases. Marker 2 was released at 55% in flavor C and flavor D while 40.8% and 33% of Marker 1 was released from flavor C and D respectively. It was estimated that enough flavor was released during the first 15-20 minutes to have antimicrobial activity based on the quantity released and the MIC results.

Example 14

Dry thyme leaves were milled on a hammermill with a 3 millimeter screen to increase the surface area and rupture the leaves. 28 kg of dry milled thyme leaves were added to 8.4 kg of water and mixed in a ribbon mixer until homogenous, about 5 minutes. The moistened thyme leaves were added to a stainless steel extraction column. Each extraction column was loaded with 28 kg dry thyme leaves. Three extraction columns were used. Liquid $CO_2$ was injected with 1 kg/hr of ethanol (96 A % natural fermentation grade), the $CO_2$ provided to the extractor at a rate of 250 kg/hr for 4 hours per extraction column under 45 atmosphere pressure at 7° C.±1°. The $CO_2$-ethanol-thyme extract was collected and passed through a heat exchanger which vaporizes the $CO_2$ to produce an ethanol-thyme extract to yield about 17% the weight of the initial leaves at this stage. The ethanol-thyme extract was processed by low vacuum distillation at 35° C. at 200 mbar to remove the ethanol in a batch still. The distilled thyme-extract was then treated on a thin-film molecular still (KD5 model, UIC GmbH of Germany) under vacuum pressure of $10^{-6}$ atmospheres at 100° C. at a flow rate of 1 kg per hour.

Example 15

An anti-microbial spray dried flavor formulation was prepared by mixing water and a starch-based encapsulating agent such as Hi-Cap 100 (National Starch, Bridgewater, N.J., U.S.A.). An oil flavor system was prepared as described in Example 3 except with the formulation according to Table 9. The oil flavor system was added to the starch and water to form an emulsion at a concentration of 16% (wt/wt) flavor system, 24% (wt/wt) Hi-Cap 100, and 60% (wt/wt) water with an average particle size of about 0.5 μm. The emulsion was then spray dried with an inlet temperature of about 160° C.

TABLE 9

| Flavor E | % material in formula | % material in final flavor system |
|---|---|---|
| Thyme Templar (THYME TEMPLAR ™, Sensient Flavor, Indianapolis, IN) | | 50% |
| Menthol crystals (Monarchy Aromatics, Ltd,) | | 0% |
| Peppermint oil (F. D. Copeland and Sons, Ltd) | | 50% |
| TOTAL | | 100% |

The final spray dried formulation was made into a volatile oil composition and analyzed with GC-MS. The chemical composition is shown in Table 10. Encapsulation of the flavor system removed water and some (about 20-60%) of the volatile oils from the formulation, resulting in about 40% load encapsulation.

TABLE 10

Anti-M Spray Dried

| Anti-microbial Compound | % |
|---|---|
| Carvacrol | 1% |
| Thymol | 12.098% |

TABLE 10-continued

Anti-M Spray Dried

| Anti-microbial Compound | % |
|---|---|
| Eugenol | 0.25% |
| Eucalyptol | 2% |
| Menthol (from peppermint oil) | 8.75% |
| Other compounds | 75.902% |
| Total | 100% |

The anti-microbial spray dried flavor formulation may be incorporated into compositions such as water, chewing gums, toothpaste, mouth rinse, liquid dentifrice, lozenges, liquid spray, and edible films.

Example 16

A breath freshening spray dried flavor formulation was prepared by mixing water and a starch-based encapsulating agent such as Hi-Cap 100 (National Starch, Bridgewater, N.J., U.S.A.). The oil flavor system as prepared and described in Example 3 (5% THYME TEMPLAR™, 40% menthol crystals, 55% peppermint oil) was added to the starch and water mixture to form an emulsion at a concentration of 16% (wt/wt) flavor system, 24% (wt/wt) Hi-Cap 100, and 60% (wt/wt) water with an average particle size of about 0.5 μm. The emulsion was then spray dried with an inlet temperature of about 160° C.

The final spray dried formulation was made into a volatile oil composition and analyzed with GC-MS. The chemical composition is shown in Table 11. Encapsulation of the flavor system removed water and some (about 20-60%) of the volatile oils from the formulation, resulting in about 40% load encapsulation.

TABLE 11

Breath Freshening Spray Dried

| Anti-microbial Compound | % |
|---|---|
| Menthol | 22.891% |
| Thymol | 1.17% |
| Eucalyptol | 0.5% |
| Carvacrol | 0.5% |
| Other compounds | 74.939% |
| Total | 100% |

The breath freshening spray dried formulation may be incorporated into compositions such as water, chewing gums, toothpaste, mouth rinse, liquid dentifrice, lozenges, liquid spray, and edible films.

We claim:
1. A method for preparing an herbal extract comprising:
   a) treating an herb with a liquid $CO_2$ extraction at a temperature of 0° C. to 10° C. and at a pressure of at least 40 atm in the presence of at least 0.1% of an alcohol to produce an alcohol-herbal extract, wherein the liquid $CO_2$ and the alcohol are applied to the herb at a flow rate of at least 150 kg/hr;
   b) distilling the alcohol-herbal extract under vacuum at a temperature of at least 20° C. to less than 60° C. to produce a first herbal extract and a residual alcohol of less than 25%; and c) distilling the first herbal extract under a pressure of at least $5 \times 10^{-4}$ mbar and at a temperature of at least 80° C. to produce a second herbal extract comprising thymol having a minimum inhibitory concentration for at least one of *Porphyromonas gingivalis, Actinomycess viscosus, Actinomyces naeslundii, Streptococcus mutans*, and *Fusobacterium nucleatum*, and the minimum inhibitory concentration being less than 0.1%.

2. The method of claim 1, wherein the alcohol comprises ethanol.

3. The method of claim 1, wherein the herb is selected from the group consisting of thyme, oregano, clove, cilantro, cinnamon, ginger, lavender, allspice, basil, bay celery seed, pimento, lemongrass, parsley, onion, mustard, tarragon, sage, rosemary, coriander, marjoram, cumin, fennel, and black peppercorn.

4. The method of claim 1, wherein step (b) is performed at a temperature of about 30° C. to about 50° C.

5. The method of claim 1, wherein the second herbal extract further comprises at least one of carvacrol, eugenol, and eucalyptol.

6. The method of claim 1, wherein the herb is selected from the group consisting of thyme, oregano, clove, allspice, and pimento.

\* \* \* \* \*